Ⓡ US008893397B2

(12) United States Patent
Ward

(10) Patent No.: US 8,893,397 B2
(45) Date of Patent: Nov. 25, 2014

(54) MONOPEDAL CLOSED CHAIN KINETIC ALIGNMENT DEVICE AND METHOD

(75) Inventor: Eric G. Ward, Aspen, CO (US)

(73) Assignee: Eric G. Ward, Aspen, CO (US)

( * ) Notice: Subject to any disclaimer, the term of this patent is extended or adjusted under 35 U.S.C. 154(b) by 708 days.

(21) Appl. No.: 13/245,571

(22) Filed: Sep. 26, 2011

(65) Prior Publication Data

US 2012/0192463 A1 Aug. 2, 2012

Related U.S. Application Data

(60) Provisional application No. 61/436,794, filed on Jan. 27, 2011.

(51) Int. Cl.
*A61F 5/14* (2006.01)

(52) U.S. Cl.
CPC ........................................ *A61F 5/14* (2013.01)
USPC ............................................. 33/515; 36/144

(58) Field of Classification Search
CPC ........................................................ A61F 5/14
USPC ............................................. 33/515; 36/144
See application file for complete search history.

(56) References Cited

U.S. PATENT DOCUMENTS 2,616,190 A * 11/1952 Darby ............................. 36/144
3,726,015 A *  4/1973 Neumann ....................... 33/3 A
4,628,936 A * 12/1986 Langer et al. .................... 36/173
4,784,143 A * 11/1988 Hebert et al. .................... 36/144
5,168,634 A * 12/1992 Misevich ......................... 33/515
5,345,701 A *  9/1994 Smith ............................. 36/144
5,689,849 A * 11/1997 Charles ....................... 12/146 M
6,564,465 B1 *  5/2003 Ward ............................. 33/515
6,845,568 B2    1/2005 Ward
7,069,665 B1 *  7/2006 Adriano ......................... 33/515
7,125,509 B1   10/2006 Smith
7,421,789 B1    9/2008 Sullivan
7,516,555 B2    4/2009 Sullivan
7,674,419 B2    3/2010 Thompson
7,685,728 B2    3/2010 Goonetilleke
7,849,612 B2 * 12/2010 Epstein .......................... 36/159
8,479,405 B2 *  7/2013 Smirman ........................ 33/534
2004/0193075 A1  9/2004 Martindale
2006/0059726 A1 *  3/2006 Song et al. ...................... 36/142
2009/0064539 A1 *  3/2009 Park et al. ......................... 36/88

* cited by examiner

*Primary Examiner* — Christopher Fulton
(74) *Attorney, Agent, or Firm* — Martensen IP

(57) ABSTRACT

A modular footbed comprised of a forefoot portion, a heel portion, a bridge and arch support can be fashion to place the knee in dynamic alignment with the femoral head of the femur and the ankle. Standing on one leg and repetitively extending and flexing the knee of the supporting leg, one can observe side-to-side deviations of the knee from a natural position. Various components of the modular footbed are incorporated so as to enable the knee to remain aligned throughout its range of motion.

29 Claims, 10 Drawing Sheets

MONOPEDAL CLOSED CHAIN KINETIC ALIGNMENT DEVICE AND METHOD

RELATED APPLICATION

The present application relates to commonly assigned U.S. Pat. No. 6,564,465 and U.S. Pat. No. 6,845,568, which are hereby incorporated by reference in their entirety for all purposes as if fully set forth herein.

BACKGROUND OF THE INVENTION

1. Field of the Invention

Embodiments of the present invention relate, in general, to footbeds, foot related orthotics, shoe and sandal technology and more particularly to methods and systems for establishing dynamic alignment of lower extremity musculature and skeletal components.

2. Relevant Background

Learning to walk is a complex skill. While most children learn to walk around 12 to 15 months of life, the learning process that makes those first steps possible begins months before. Around 4 months babies begin to control head and neck movement. Shortly thereafter they can roll from side to side by gaining control of their torso and by 6 months are able to roll completely over.

In a few months more, a child can sit upright and somewhere between 6-9 months babies begin to make attempts to crawl. With all of these skills mastered an infant can make the next major leap of standing and then walking. Within a few months of waddling, a mobile toddler soon becomes capable of a full out sprint.

This process is so natural that the complexity of walking or running is underappreciated. The human motion of walking is controlled by the neuro-muscular system. But bipedal walking and running requires not only an understanding of the neuro-muscular control system but an appreciation for several mechanical parameters (lengths, mass, distributions) as well.

From a simplistic point of view the bipedal motion of walking is akin to the motion of a pendulum. A pendulum is a device that transforms kinetic energy of motion into potential energy, and then back into kinetic energy. As the pendulum moves through the bottom of its arc the pendulum's velocity and thus its kinetic energy reaches a maximum. Thereafter that kinetic energy is converted back to potential energy as the pendulum comes to rest at its peak. With each step the human body becomes an inverted pendulum. But while a pendulum is incredibly efficient, the human body has some restrictions. One such restriction is when the arm of that pendulum, i.e. the leg, is not perfectly aligned.

An individual standing upright is a very stable structure. The triangle that is formed between the two legs, hip girdle and ultimately through the torso is a very stable geometric structure. The transverse extension of each foot with respect to the geometric plane formed by the two legs further stabilizes the structure. Indeed an individual standing still with their legs shoulder width apart represents a very stable and strong structure.

In such a configuration a knee that is perfectly aligned has its load-bearing axis on a line running down the middle of the leg, through the hip, knee and ankle. In a static configuration this line exists in what is referred to as the coronal or frontal plane. The coronal plane divides the body lengthwise, anterior from posterior, such that the face is separated from the back of the head, the chest from the back, the palms from the back of the hands, and the shins from the calves. But when walking, the body performs a pendulum motion about the sagittal plane. The sagittal plane bisects the left and right sides of the body longitudinally. This plane runs down the center of the head, torso and between the legs and feet.

As an individual walks or runs the neuro-muscular "control system" maintains a consistent center of gravity by shifting weight from one side of the sagittal plane to the other. In essence when you walk (or run) you lean and rest on one of your pendulums while repositioning the other. The problem lies in the fact that our pendulums are not so perfect.

Normally the outside part of the heel makes initial contact with the ground as an individual walks or runs. The foot rolls inward as it comes in complete contact with the ground where it can support the entire body weight. The rolling in of the foot optimally distributes the forces of impact. This movement is critical to proper shock absorption and a moderate amount of pronation, as defined herein, is required for the foot to function properly.

In a related condition called underpronation, as the outside of the heel makes initial contact with the ground the inward movement of the foot rolls less than for those with normal or flat feet. Consequently, forces of impact are concentrated on a smaller area of the foot (the outside part), and are not distributed as efficiently as with normally pronation.

Supination is the opposite of pronation and refers to the outward roll of the foot during normal bipedal motion. A natural amount of supination occurs during the push-off phase of running, and to a lesser extent during a walking gait as the heel lifts off the ground and the forefoot and toes are used to propel the body forward.

Pronation and supination, as they are classically understood, attempt to describe a complex three dimensional movement of the skeletal and neuromuscular structure of the foot. Other terms such as inversion vs. eversion, plantar flexion vs. dorsiflexion, and abduction vs. adduction describe various aspects of the complex task of bipedal motion. The dynamic interaction between the skeletal structure of the foot and its neuromuscular counterparts is very complex. For example, pronation is a skeletal collapse of the foot that is arrested by the surrounding musculature. Supination is thus the muscular over-reaction or over bias to the structural collapse. Moreover, while the musculature biases the foot toward supination the skeletal structure biases the foot to underpronation. To efficiently and effectively achieve bipedal motion a balance between the cyclical activities of both pronation and supination must occur.

The interaction of the skeletal and neuro-muscular systems involved in walking and running is impeded when proper foot, ankle and knee alignment is not maintained. Unlike the very stable structure of an individual standing still with their legs spread, walking and running is inherently unstable and any misalignment of the mechanical components requires neuro-muscular compensation. The compensation requires energy and reduces overall endurance. Lastly, misalignment can ultimately result in injury and chronic pain.

There are many orthotic devices and supplemental footbeds designed to modify and correct misalignment of the knee, ankle and foot. Each, however, fails to consider the dynamic nature of bipedal motion. Moreover, misalignment issues vary from individual to individual and from one extremity to the other. Accordingly a preformed orthotic insert is not capable of addressing all of the varying corrective needs consistently or adequately. These and other deficiencies of the prior art are addressed by one or more embodiments of the present invention.

SUMMARY OF THE INVENTION

Disclosed hereafter, according to one embodiment of the present invention, is a method for lateral dynamic alignment of the hip, knee, ankle and foot. Dynamic deviations in alignment of an individual's knee are observed as the individual repetitively extends and flexes their knee while standing on one foot. In a motion akin to a single leg squat the deviation of the knee from a neutral position is observed while various forms of forms of modular alignment devices are placed under the supporting foot. The modular devices are configured and positioned so as to place the knee in alignment with the femoral head of the femur and the ankle throughout the range of motion of the knee. Each leg is investigated and corresponding footbed developed independently.

According to another embodiment of the present invention a modular footbed is comprised of a forefoot portion, a heel portion, a bridge and an arch support. Each of the forefoot portion and the heel portion include a plurality of wedges of varying inclinations. According to one embodiment of the present invention the inclinations can vary symmetrically across the wedge while in other embodiments the inclination can be asymmetric. The combined inclination of the plurality of wedges matches the necessary correction to place the limb into neutral alignment. The inclination developed by the forefoot portion is independent of that of the heel portion.

According to another embodiment of the present invention the various components of the modular footbed are nested so as to provide lateral structural support yet provide for versatility to meet individual needs. The bridge couples the forefoot portion to the heel portion and provides a platform on which a modular arch support can reside.

The features and advantages described in this disclosure and in the following detailed description are not all-inclusive. Many additional features and advantages will be apparent to one of ordinary skill in the relevant art in view of the drawings, specification, and claims hereof. Moreover, it should be noted that the language used in the specification has been principally selected for readability and instructional purposes and may not have been selected to delineate or circumscribe the inventive subject matter; reference to the claims is necessary to determine such inventive subject matter.

BRIEF DESCRIPTION OF THE DRAWINGS

The aforementioned and other features and objects of the present invention and the manner of attaining them will become more apparent, and the invention itself will be best understood, by reference to the following description of one or more embodiments taken in conjunction with the accompanying drawings, wherein.

Figure 1A:
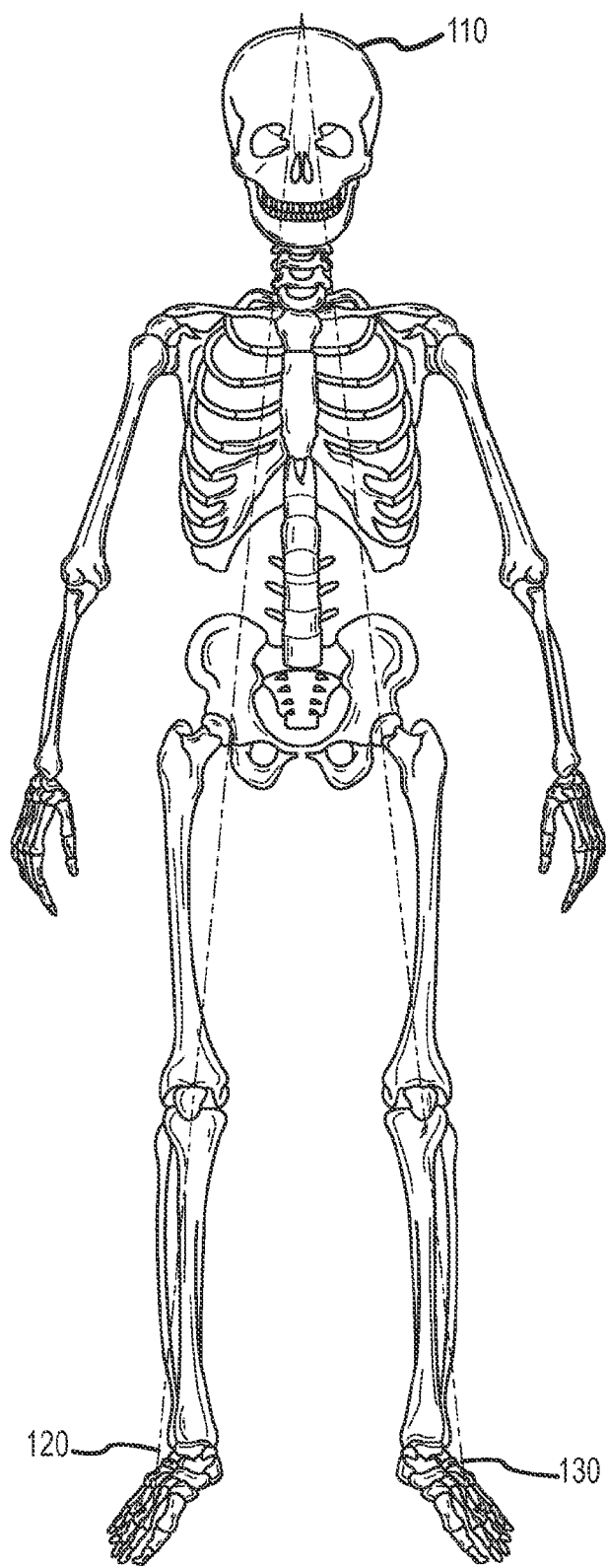
FIGS. 1a and 1b show front and side skeletal views of the human body.

The Figures depict embodiments of the present invention for purposes of illustration only. One skilled in the art will readily recognize from the following discussion that alternative embodiments of the structures and methods illustrated herein may be employed without departing from the principles of the invention described herein.

DEFINITIONS

Flexion—Bending movement that decreases the angle between two parts. Bending the knee, or clenching a hand into a fist are examples of flexion. When sitting down, the knees are flexed.

Extension—The opposite of flexion; a straightening movement that increases the angle between body parts. In a conventional handshake, the fingers are fully extended. When standing up, the knees are extended. Extension of the hip or shoulder moves the limb backward (towards the posterior side of the body). The muscles that extend the knee are the quadriceps.

Abduction—A motion that pulls a structure or part away from the midline of the body (or, in the case of fingers and toes, spreading the digits apart, away from the centerline of the hand or foot).

Adduction—A motion that pulls a structure or part towards the midline of the body, or towards the midline of a limb. Dropping the arms to the sides, or bringing the knees together, are examples of adduction. In the case of the fingers or toes, adduction is closing the digits together.

Internal rotation (or medial rotation) of the shoulder or hip would point the toes or the flexed forearm inward (towards the midline).

External rotation (or lateral rotation) is the opposite of Internal Rotation. It would turn the toes or the flexed forearm outward (away from the midline).

Pronation—A rotation of the ankle that moves the foot from an anterior-facing position to a posterior-facing position. For the foot, pronation will cause the sole of the foot to face more laterally than when standing in the anatomical position. Normal pronation comprises three-dimensional movement encompassing the full range of motion from both subtalor and the dorsal side of the talus bone.

Supination—The opposite of pronation, the rotation of the ankle so that the foot faces anteriorly. Supination in the foot occurs when a person appears bow-legged with their weight supported primarily on the anterior of their feet. In running, supination (also referred to as underpronation) is the insufficient inward roll of the foot after landing.

Dorsiflexion—Extension of the entire foot superiorly, as if taking one's foot off an automobile pedal.

Plantarflexion—Flexion of the entire foot inferiorly, as if pressing an automobile pedal. Occurs at the ankle.

Medial—describes a structure toward the midline of the body and lateral away from that median plane. Intermediate describes a structure between a medial and a lateral structure. The nose is medial to the ears while the ears are lateral to the nose.

Lateral—In anatomy, the side of the body or a body part that is farther from the middle or center of the body. Typically, lateral refers to the outer side of the body part, but it is also used to refer to the side of a body part. For example, when referring to the knee, lateral refers to the side of the knee farthest from the opposite knee.

Eversion—the movement of the sole of the foot away from the median plane.

Inversion—the movement of the sole towards the median plane (same as when an ankle is twisted).

Valgus—In orthopedics, a valgus deformity is a term for outward angulation of the distal segment of a bone or joint. The opposite deformation, medial deviation of the distal bone, is called varus.

Varus—In orthopedics, a varus deformity is a term for the inward angulation of the distal segment of a bone or joint. The opposite of varus is called valgus.

DESCRIPTION OF THE INVENTION

A method and associated modular device for lateral alignment are hereafter disclosed by way of example. As an individual walks or runs and the knee and ankle travels through various states of flexion and extension, the transfer of weight and energy between the various components of the leg can be detrimentally affected due to misalignment. In a normal circumstance, as the knee is flexed the patella translates along a vertical line from the hip socket/femoral head to the ankle and foot. This neutral alignment configuration enable a maximal transfer of weight and energy through the rigid structure of the bones making walking and running relatively efficient. However, when during this process of flexion and extension the knee translates medially inward (varus) or laterally outward (valgus) the musculature surrounding the hip, knee, ankle and foot operate to maintain balance and stability. These efforts can be exhaustive leaving the skeletal and neuro-musculature system vulnerable to injury or otherwise limiting an individual's mobility. Various embodiments of the present invention recognize the complexity and interaction of the hip, knee, ankle and foot to identify, detect, measure and analyze misalignment conditions so that a device can be fashioned to place otherwise misaligned extremities into alignment.

Embodiments of the present invention are hereafter described in detail with reference to the accompanying Figures. Although the invention has been described and illustrated with a certain degree of particularity, it is understood that the present disclosure has been made only by way of example and that numerous changes in the combination and arrangement of parts can be resorted to by those skilled in the art without departing from the spirit and scope of the invention.

The following description with reference to the accompanying drawings is provided to assist in a comprehensive understanding of exemplary embodiments of the present invention as defined by the claims and their equivalents. It includes various specific details to assist in that understanding but these are to be regarded as merely exemplary. Accordingly, those of ordinary skill in the art will recognize that various changes and modifications of the embodiments described herein can be made without departing from the scope and spirit of the invention. Also, descriptions of well-known functions and constructions are omitted for clarity and conciseness.

The terms and words used in the following description and claims are not limited to the bibliographical meanings, but, are merely used by the inventor to enable a clear and consistent understanding of the invention. Accordingly, it should be apparent to those skilled in the art that the following description of exemplary embodiments of the present invention are provided for illustration purpose only and not for the purpose of limiting the invention as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

By the term "substantially" it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

One aspect of the present invention is a method for determining dynamic angular misalignment of an individual's leg. According to one embodiment of the present invention, as an individual balances on one foot and flexes and extends the knee of the supporting leg, side-to-side movement of the knee is observed and measured. As an individual proceeds through the motion of what is akin to a single leg squat, as viewed from the front of the body, the vertical sagittal track of the knee can be observed and compared to a base line running from the femoral head to the ankle. Said differently, the present invention compares the projected track of the knee on the ground to a reference line running from the ankle to the middle of the foot. The question becomes whether that projected line is parallel with the reference line or does it deviate. According to yet another embodiment of the present invention the hip socket (femoral head) is positioned over a base of support, while standing on one leg, during flexure and extension of the knee. This hip placement also aids in determining proper dynamic mono-pedal alignment.

Figure 1B:
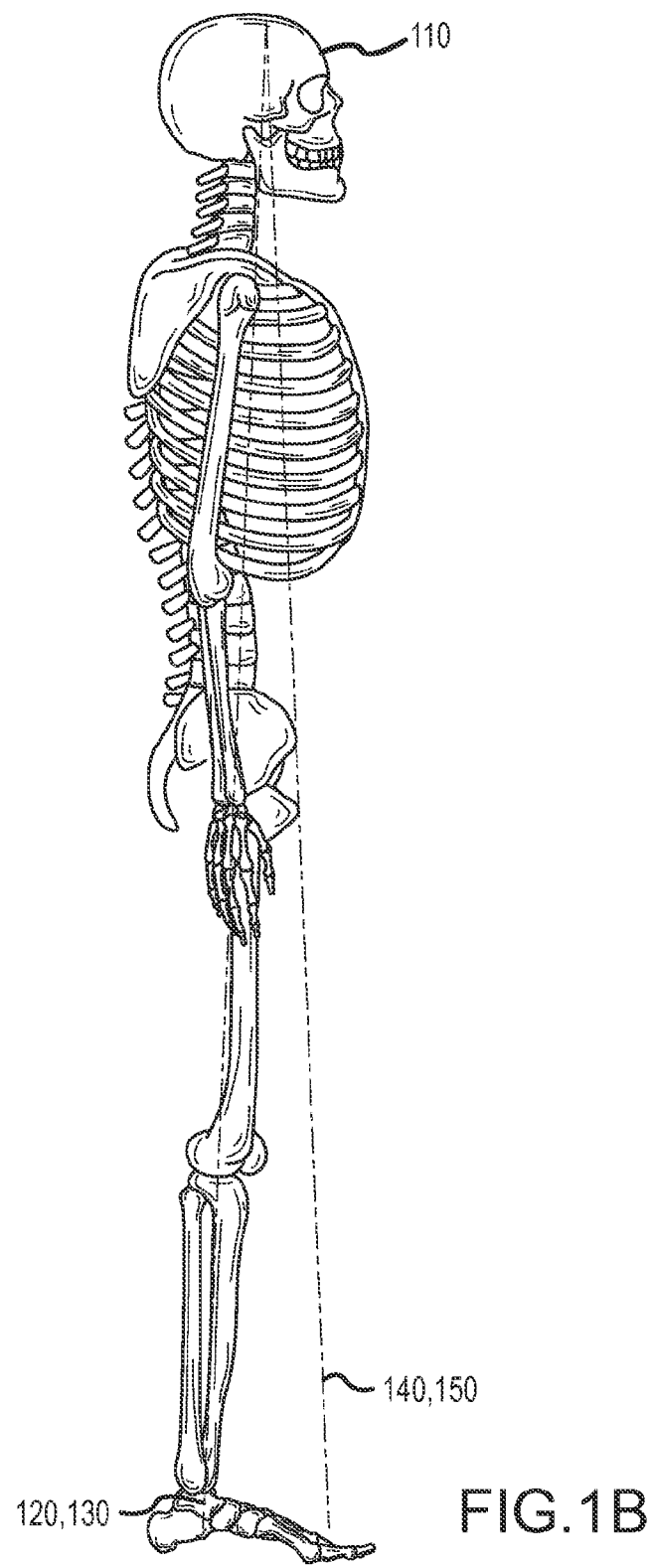

FIGS. 1a and 1b depict a front and side skeletal view of a human being respectively. Looking first at the front view depiction of FIG. 1a, when a person stands with their feet shoulder width apart a triangle is formed with one vertex 110 near the head and the other two vertices 120, 130 located at each foot. From a geometrical point of view the triangle formed is a very stable structure. In a static condition with the weight being efficiently transferred to the skeletal frame a person can support much more than his or her own body weight. Understandably, laterally (from side to side) the human body is very stable.

The same sort of geometric triangle, albeit on a smaller scale, is formed with respect to forward and rearward motion. As shown in FIG. 1b a triangular structure is formed between the same vertex near the head 110 and one found near the heel 120, 130 and forefoot 140, 150. Indeed each lower vertex 120, 130 of the structure shown in FIG. 1a includes at least one corresponding vertex near the forefoot of each foot. The additional points of support transform the triangle shown in FIG. 1a to a pyramidal type of structure.

Figure 2:
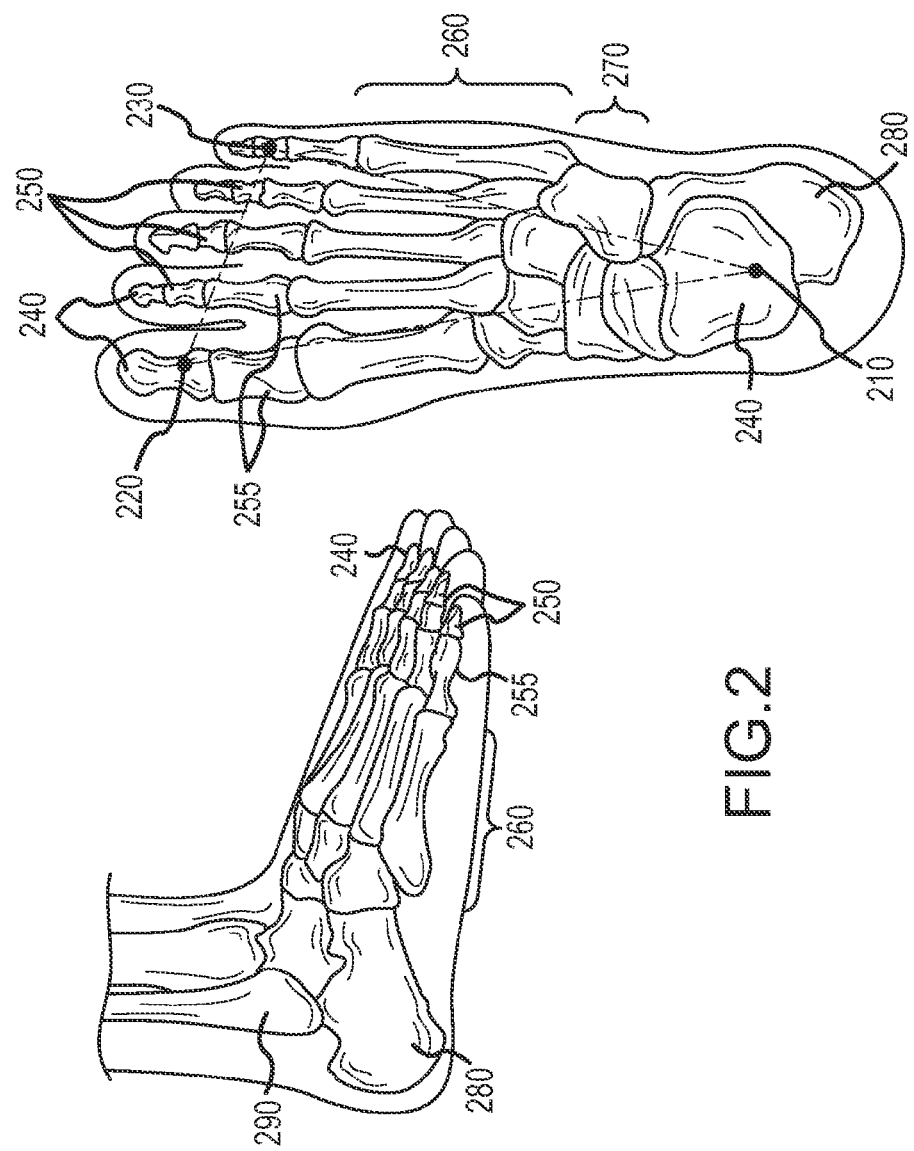
FIG. 2 shows a side and top view of the musculature and skeleton of a human foot.

The static and dynamic support system of the human body becomes even more stable when one considers the complexity and design of the human foot. The human foot is comprised of numerous individual bones and musculature. As will be appreciated by one of reasonable skill in the art, the interactions of each bone and points of contact of the foot is beyond the scope of this application. However, it can be appreciated that in a static condition the human foot forms a platform on which the remainder of the human skeleton rests. FIG. 2 presents a side and top view of a human foot as would be known to one of reasonable skill in the relevant art.

As with FIG. 1, the primary points of contact of the human foot shown in FIG. 2 depicts a stable geometric structure. The construction of the leg-ankle-foot interface conveys loads to three primary points of contact. The heel 210 resides essentially under the juncture of the tibia and fibula. The forefoot includes a plurality of bones (distal 240, middle 250 and proximal 255 phalanx bones or toes) which form the other two vertices; a vertex located near the ball of the foot and big toe or first metatarsal head, and the other at the outside of the foot near the juncture of the metatarsal bones 260, tarsal bones 270 and outside most phalanx or the fifth metatarsal head. These three vertices form the triangular base of a pyramid whose apex is the talus bone. Through a complex network of structural bones and musculature the foot provides a support system to the talus bone 290 in conjunction with the calcaneus bone 280 and thereafter the femur and tibia. Three ligaments connected to both the talus 290 and calcaneus 280 known as the sinus tarsi provide the necessary sensory information for an individual to maintain balance.

It is only by examining lateral alignment while extending and flexing the leg while balancing on one foot that the true dynamic and cyclical nature of balancing during bipedal motion can be examined. The advantages of the stable geometric structures described above are significantly diminished when a misalignment occurs. To properly understand the features of the present invention it is important to appreciate the various misalignment maladies that can occur and how they can significantly impact something as simple as walking, running or even standing.

Figure 3:
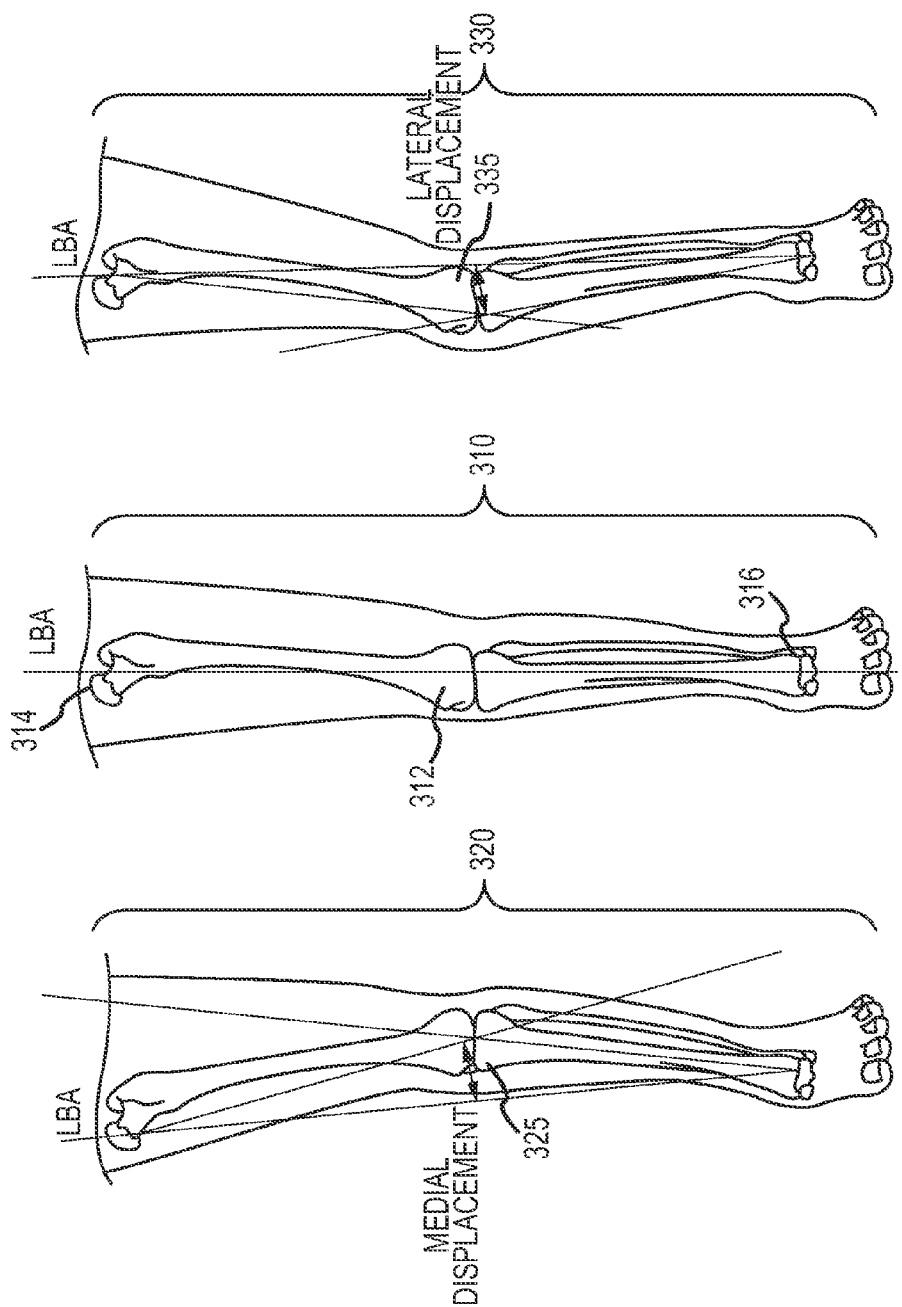
FIGS. 3a-3c present a frontal view of three side-by-side depictions of varus, neutral and valgus deviations of the knee.

As was previously mentioned under normal circumstances the femur, knee structure, tibia and fibula combination, ankle and foot interface and extend and flex in alignment. For the purposes of this disclosure, neutral alignment is understood to describe movement of the patella along a line originating from the hip socket and extending to the heel of the foot. FIG. 3 shows three renditions of a leg in various states of alignment. A neutral relationship 310 between the components of the leg is shown in the center rendering. In this case the central juncture 312 between the femur and tibia resides on a line drawn from the femoral head 314 to the talus (heel) 316.

The left most depiction in FIG. 3 shows a varus deformation 320 of the knee. In this case the distal segment of the leg, the tibia and fibula deviates medially 325 from the proximal segment, the femur. The right most depiction in FIG. 3 depicts a knee in a state of valgus deformation 320. In this case the distal portion of the leg, the tibia and fibula, are laterally deviated 335 with respect to the proximal portion, the femur.

A condition of valgus or varus deformation of the lower extremities is well known. Indeed the common knock-knees or bow legged condition are common language descriptions of this malady due to structural (skeletal) deformations. What is less understood and appreciated is how this sort of deformation can occur during the dynamic action of the leg and how a managed interaction of the ankle and foot can dramatically impact a neutral alignment.

Figure 4:
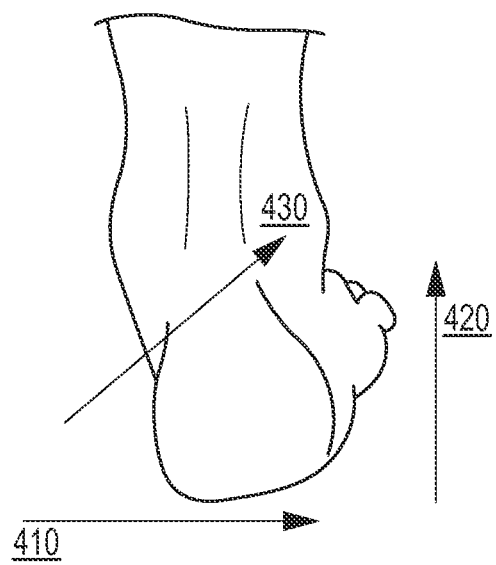
FIG. 4 depicts a right rear perspective view of a human foot and motions associated with pronation.

Normally the outside part of the heel is the first part to make contact with the ground as an individual walks or runs. The foot "rolls" inward about fifteen percent as the remaining foot comes in complete contact with the ground so as to support the body weight of an individual without any problem. The rolling in of the foot optimally distributes the forces of impact. This movement is called "pronation," and it is critical to proper repetitive shock absorption. FIG. 4 shows a posterior view of a left foot in a pronation movement. As the heel comes into contact with the surface a medial force drives the foot inward 410 and upward with a resultant force 430 being constrained by the mucluature. A moderate amount of pronation is required for the foot to function properly, however damage and injury can occur during excessive or inadequate pronation. When excessive pronation does occur the foot arch flattens out and stretches the muscles, tendons and ligaments underneath the foot.

In underpronation the outside of the heel makes initial contact with the ground but the inward movement of the foot occurs at less than fifteen percent (i.e., there is less rolling in than for those with normal or flat feet). Consequently, forces of impact are concentrated on a smaller area of the foot (the outside part), and are not distributed as efficiently.

Figure 5:
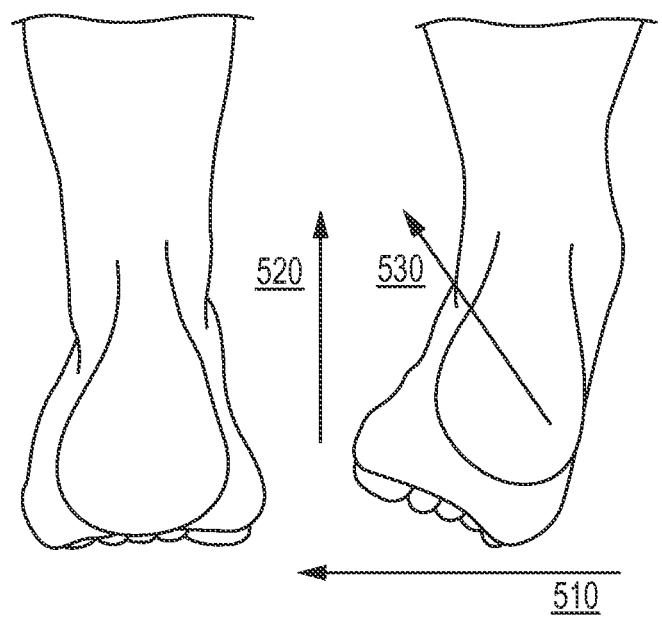
FIG. 5 is a rear view of a foot experiencing supination and a foot experiencing underpronation.

Supination, as shown in FIG. 5, is the opposite of pronation and refers to the outward roll of the foot during normal motion. As the foot comes into contact with the ground an outward force 510 drives and rolls the foot upward 520 resulting in a lateral displacement 530. A natural amount of supination occurs during the push-off phase of the running, and to a lesser extent walking, gait as the heel lifts off the ground and the forefoot and toes are used to propel the body forward. However, excessive supination (outward rolling) can place a large strain on the muscles and tendons that stabilize the ankle, and can lead to the ankle rolling completely over, resulting in an ankle sprain or total ligament rupture.

Figure 6:
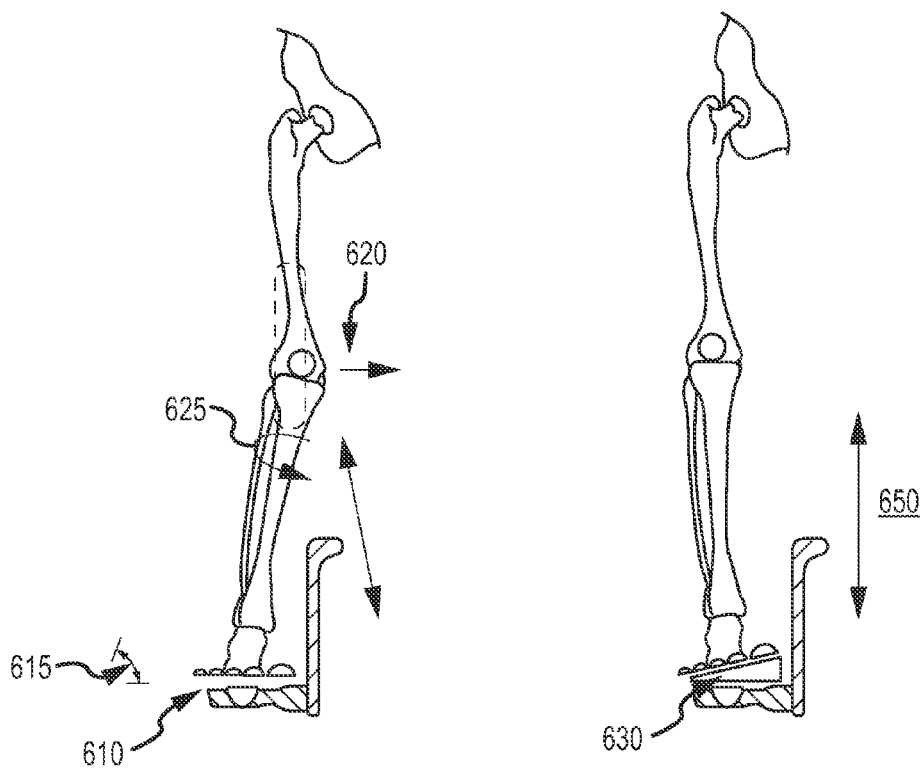
FIG. 6 depicts the use of a modular footbed to correct a medial dynamic deviation of the knee according to one embodiment of the present invention.

The interaction between the various maladies of the ankle (underpronation or supination) and that of the knee (varus and valgus) are illustrated in FIG. 6. FIG. 6 shows the effect of a modular footbed according to one embodiment of the present invention correcting what would otherwise be a medial deviation of the knee.

In the present example an individual's foot is shown having a varus forefoot deviation. As one of reasonable skill in the applicable art would understand the majority of individuals affected with a forefoot variation experience a varus deviation. When an individual with this sort of malady steps down the bottom of the foot mates with the ground placing the ankle at an angle 615. The angle of impact 615 drives the knee, in this case, inward 620, or medially displaces the distal portion of the lower leg. As the knee deviates it can also rotate 625 placing additional stress and strain on the musculature surrounding the skeleton. Anterior Tibialus and posterior tibialus are the main supinating muscles. These two muscles are approximately 5 times stronger than the three opposing muscle groups. The lack of balance in the strength of the opposing musculature points to the skeletal bias in the opposite direction. Thus a properly functioning system uses the opposing biases of the skeleton and musculature to achieve efficient bipedal motion.

According to one aspect of the present invention, to compensate for the varus state of the foot a modular footbed 630 matching the varus condition is placed under the foot as shown in the rightmost portion of FIG. 6. With the modular footbed in place the ankle is reoriented so as to be in dynamic alignment with the knee and femoral head. As the individual's knee travels through various states of flexion and extension the knee maintains its alignment 650.

The example shown in FIG. 6 illustrates the effects of valgus and varus deviations but does not consider pronation or supination. The dynamic nature of pronation necessitates the recognition that the foot is flexible. In the previous example the varus angle of the foot was considered constant and planar. For example FIG. 6 shows the varus foot at an angle tilting up to the inside from the little toe to the big toe. Lacking in this depiction is any consideration that the angle of tilt may vary longitudinally (in this case in and out of the page) along the length of the foot.

According to one embodiment of the present invention a modular footbed is placed under a foot having either a varus or valgus deviation. The various components of the footbed are crafted to match angular variations along the length of the foot to address pronation complications as well as valgus or varus deviations.

Figure 7:
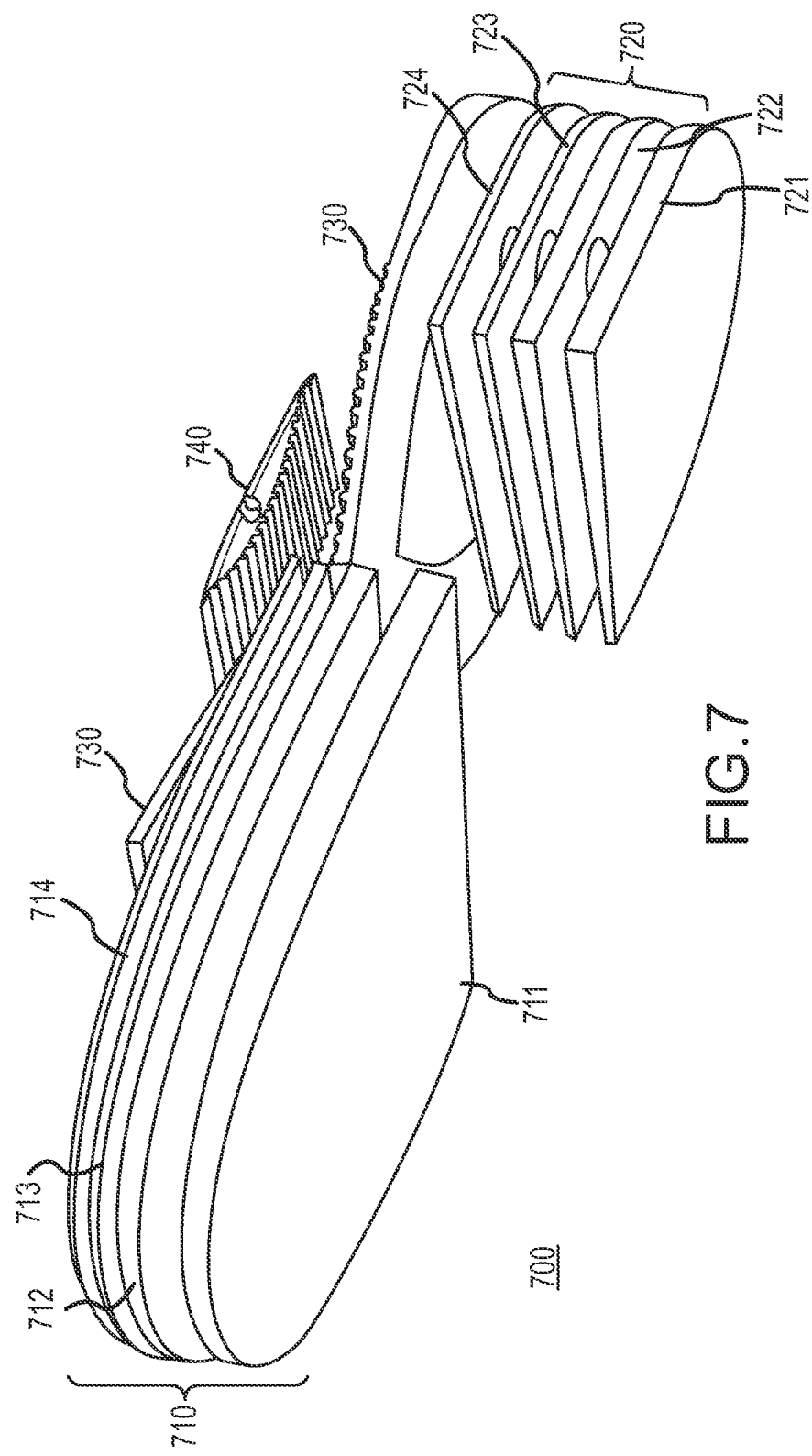
FIG. 7 is a right lower perspective view of an exploded modular footbed according to one embodiment of the present invention.

FIG. 7 shows a bottom left perspective view of a modular footbed 700 according to one embodiment of the present invention. Each modular footbed is comprised of a forefoot portion 710, a heel portion 720, a connecting bridge 730 and an arch support 740.

One aspect of the present invention is that the forefoot and the heel portions are comprised of a plurality of angular footbeds that can be independently interchanged to provide an overall angular insert. In one embodiment of the present invention the combination of the wedges of the forefoot can vary as compared to that of the heel. In the present example the forefoot portion 710 and the heel portion 720 each include four individual wedge components. Each component possesses an angular characteristic that when combined compensates for an individual's deviation.

For example, the lowest wedge of the forefoot 711 may possess a lateral outward inclination of 2.0 degrees meaning that the outward or lateral portion of the wedge as viewed from the front is thicker than the inner or medial portion. The next wedge 712 may possess a 1.5 degree lateral outward inclination and the final two wedges 713, 714 may possess no inclination at all. Thus, each of the plurality of wedges can possess its own angular characteristics. In this example the forefoot was determined to possess a 3.5 valgus tilt. To correct such an inclination the combination of the wedges must equal a complementary 3.5 degrees in a varus direction. By doing so the forefoot interacts with the ground in a manner such that the ankle is in alignment with the femoral head. As will be appreciated by one of reasonable skill in the relevant art the number of wedges can vary. While in this example the forefoot portion 710 was comprised of four wedges, other implementations of the present invention, and in other embodiments, more or less wedges can be utilized. The present invention provides a modular approach that can be applied to a variety of angular needs.

Another aspect of the present invention is that the amount of angular deviation generated by forefoot wedges 710 can differ from that of the heel portion 720. The human foot is not a rigid fixture, nor is its characteristics consistently planar. Rather than having a single wedge or even a combination of wedges that travel from the forefoot to the heel at a consistent angle, the present invention recognizes the need in some circumstances to vary the angular correction of the device. According to one embodiment of the present invention the angular correction at the heel is independent of that formed in the forefoot.

In the present example shown in FIG. 7 four wedges comprise the heel portion 720 of the modular footbed. Again, the number of wedges in each portion of the footbed can vary as necessary to meet the needs of the individual. As with the forefoot portion 710 each wedge 721, 722, 723, 724 can be of a varying degree of inclination. Assume for this example that the individual requires for this foot a 3.5 degree varus correction in the forefoot but a 5.0 degree varus correction at the heel. One of reasonable skill in the relevant art will recognize that these numbers may vary and that the present illustration is but one exemplary means by which to address the deviation.

Using wedges having predetermined angular characteristics, a heel portion totaling a varus correction of 5.0 degrees can be constructed. In one implementation the lower wedge 721 can have a 0.5 degree lateral inclination. The second wedge 722 can also possess a 0.5 degree lateral inclination while the third wedge possesses a varus inclination of 1.0 degrees. With two additional 2 degree shims, a 5 degree lateral correction is formed that possesses a consistent lateral thickness.

Once the forefoot portion 710 and the heel portion 720 have been constructed they are joined by a bridge 730. The bridge not only mechanically couples the two portions together so as to maintain proper positioning relative to each other but also provides a means to convey forces from the heel to the forefoot and from the forefoot to the heel. Resting on top of the bridge 720, in one embodiment, is a modular arch support 740.

According to another embodiment of the present invention the arch support 740 can be custom fit so as to provide optimal support under the arch of the foot as well as be positioned forward or aft on the footbed. And as shown in subsequent drawings, the arch can also be positioned laterally on the bridge to again meet varied needs of an individual.

Another aspect of the present invention is that the overall thickness of the forefoot portion can be different than that of the heel portion. Moreover the thickness can vary from front to back to provide a stable yet variably thick footbed. For example and as shown in FIG. 7, the forefoot portion of the footbed 710 is comprised of four wedges 711, 712, 713 714. Similarly, the heel portion of the footbed 720 is also comprised of four wedges 721, 722, 723, 724. As previously discussed each portion can provide an independent inclination correction. In addition however the overall thickness of the wedges, in this case the combined four wedges, can differ. For example if it is determined that an individual, in addition to the need for a varus correction, requires an inclination correction or a variance in the thickness of the footbed from front to aft, the various components of the forefoot and the heel portion can be varied to accommodate that need.

Consider the situation where in addition to the need to correct a valgus deviation using a varus footbed, the individual requires a 1.0 degree inclination with the forefoot portion being higher than the heel portion. According to one embodiment of the present invention the modular wedges of the foot bed can be compiled so that the overall thickness of the forefoot portion exceeds that of the heel portion. In the previous example at least one of the four wedges was planar or flat (having no inclination characteristics). To provide an inclination variation along the longitudinal axis of the footbed the thickness of one of these flat wedges can vary to result in the needed inclination. In other embodiments in which all of the wedges possess some aspects of inclination the base thickness of one or more wedges can vary to achieve the same result.

According to another embodiment the thickness of one or more of the wedges vary along the longitudinal length of the wedge. While maintaining the concept of having the thickness of the forefoot portion vary as compared to the heel portion, the thickness further varies within the forefoot and/or heel portion itself.

Turing back to FIG. 7, the forefoot portion is comprised of four wedges 711, 712, 713, 714. As previously discussed the two bottom 711, 712 wedges possess a lateral inclination totaling 3.5 degrees. The lateral thickness of the remaining two wedges 713, 714 is consistent. According to one embodiment of the present invention one or more of the wedges 713, 714 can possess a longitude thickness variation so as to provide the combined forefoot portion 710 with both a lateral inclination and a longitudinal inclination.

Figure 8:
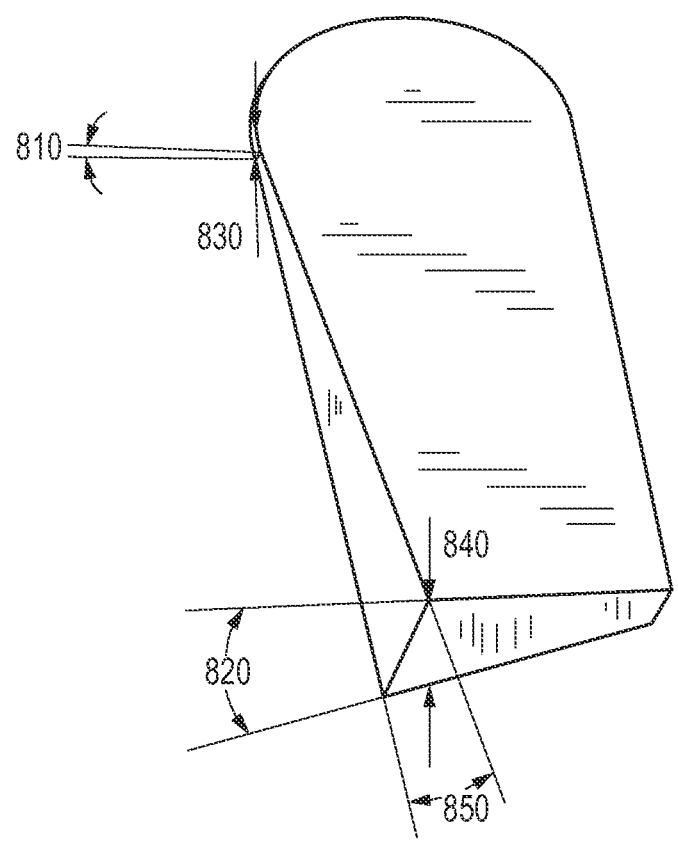
FIG. 8 is a right forward perspective view of an asymmetric component of a modular footbed according to one embodiment of the present invention.

FIG. 8 depicts an exemplary footbed wedge possessing asymmetric inclination characteristics according to one embodiment of the present invention. In addition to the modular approach described above, another aspect of the present invention is to have one or more wedges in either the forefoot or heel portion that individually possesses asymmetric variations in thickness, and thus inclination. The wedges can be configured to address both a lateral/medial deviation as well as an anterior/posterior deviation issue using one or more components. Moreover, a full footed wedge possessing varying inclination from side-to-side and front-to-back can be used in place of or in combination with the modular design.

In this example the wedge provides a variable lateral inclination from 0.5 degrees at the front of the wedge 810 to 1.0 degrees at the aft portion of the wedge 820. In this example the variation of the thickness is linear, however, as one skilled in the relevant art will appreciate, the variation of thickness can take many forms beyond a simple linear variation.

In addition to the lateral variation of the wedge, the wedge also illustrates variability in longitudinal thickness. As shown the thickness of the forward portion of the wedge 830 is thinner than the aft portion 840. In this case variation of the wedge approximates a 1.0 degree 850 forward to aft inclination.

Yet another aspect of the present invention is the ability to provide different thickness of top sheet material so as to lift one foot as compared to the other without any fore/aft or lateral change. This allows the device of the present invention to accommodate a leg length discrepancy from right to left.

Another aspect of the present invention is to reduce the thickness of the footbed near the point of toe/shoe interaction without sacrificing any angular correction imparted by the footbed. One deficiency of the prior art is its failure to consider the interaction of the toes and shoes during running and walking. Adding additional material to the sole of a shoe can result in the toes interacting with the upper surface of the shoes. If there is not sufficient room in the shoe, especially at the point where the toe of the shoe creases, the toes can be impinged. Such an impingement condition is not only painful but can result in injury and ultimately defeat the corrective features of the footbed.

According to one embodiment of the present invention, the thickness of the forefoot portion of the footbed is minimized at the point at which the proximal phalanx bones (toes) interface with the metatarsal bones. By minimizing the thickness of the forefoot portion at this point the footbed maintains adequate space in the shoe so that there is no detrimental interaction between the toes and shoes during walking or running. Significantly this reduction in the thickness of the forefoot portion of the footbed at the crease point does not alter the ability of the footbed to provide an inclination solution. The forefoot portion, through its modular design, can still provide lateral/medial inclination corrections as well as longitudinal anterior/posterior corrections.

Another aspect of the present invention is the nested nature of the modular components of the footbed. As the footbed is comprised of a plurality of components, each of these components must be securely affixed to each other to form a stable footbed. Yet the junctures must be flexible enough to allow for quick modifications and adjustments without interfering with the footbed's functionality.

According to one embodiment of the present invention, each surface of the individual wedges includes opposing male/female features that allows the various wedges to interlock providing a secure two dimensional interface. As one of reasonable skill in the relevant art can appreciate the various components of the footbed are subjected to multiple lateral forces during use. The nested features of the components of the present invention prevent the various components from shifting either laterally or longitudinally during walking or running. While the footbed receives considerable compressive forces of varying intensity it does not experience forces that would tend to separate the components vertically. Thus the nested design enables the footbed to remain secure during use but yet enable the footbed to be fashioned and modified quickly and efficiently.

Figure 9:
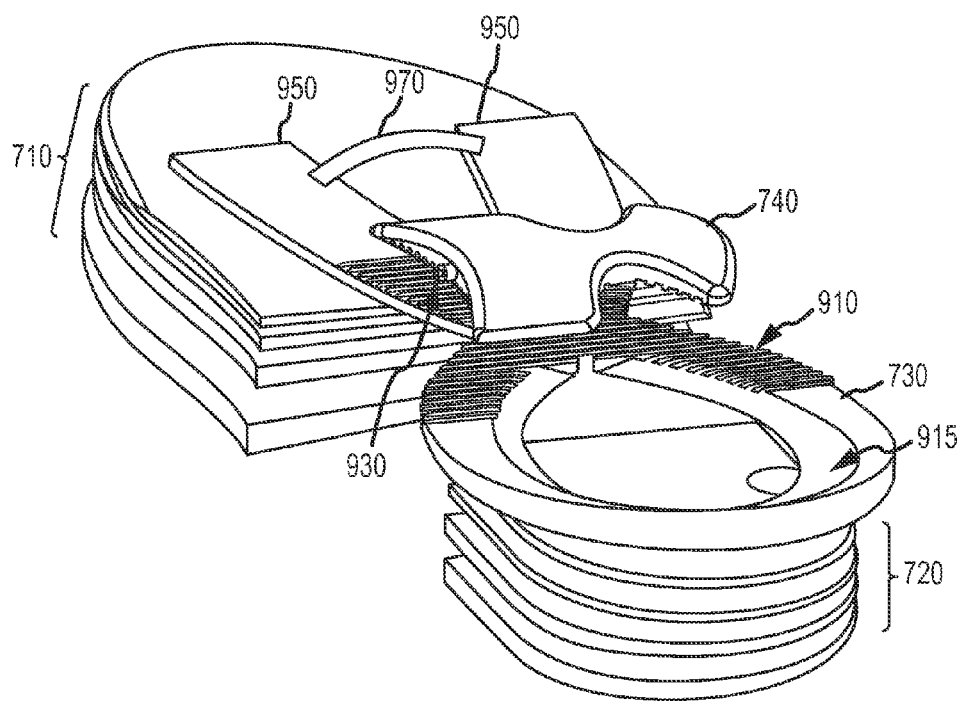
FIG. 9 is a left upper perspective view of an exploded modular footbed according to one embodiment of the present invention.

FIG. 9 shows a top view of a modular footbed according to one embodiment of the present invention. On top of the forefoot portion 710 and heel portion 720 rests the bridge 730. The bridge 730 couples the forefoot portion 710 to the heel portion 720 forming the footbed 700. The design of the bridge 730 mimics and interfaces with the three primary points of contact of the foot. The forward portion of the bridge includes two arms 950 that spread laterally so that one arm rests under the inner portion of the forefoot (under the big toe) and the other arm spreads laterally outward resting under the outer portion of the forefoot or little toe. The two arms 950 of the bridge 730 converge to a central portion, merge and then form a circular receptacle 915 at the heel. The circular portion 915 is crafted to accept and stabilize the heel over the heel portion 720 of the footbed. The bridge 730 acts not only to position the forefoot portion 710 correctly with respect to the heel portion 720, but also to consistently convey loads from the individual to the footbed. The cradling effect of the heel portion 915 and the two points of contact in the forefoot provide the foot with a natural and stable walking surface.

There should also be some mention of the adjustable transverse arch shape in the bridge. It will be either heat moldable or extra metetarsal pads will be made to create this shape under the fore foot arch.

According to one embodiment of the present invention the upper surface of the bridge 910 includes a serrated or channeled structure traversing the bridge. These channels mate with corresponding ridges found on the underside of the arch support 740. The channel/ridge juncture of the bridge 730 with the medial arch support 740 allows the arch support to be positioned forward and aft along the bridge as well as from side to side.

Moreover and according to another embodiment of the present invention, the modular medial arch support comprises an inflatable vessel. Through an access port 930 the arch support can be enlarged or reduced to meet the needs of individuals having a low or high arch. As feet vary in size and shape the present invention can accommodate a plurality of sizes and shapes of arch support and each can be custom fit to the individual's needs.

Another feature of the present invention is a metatarsal arch support 970 that can be positioned between the two forward arms 950 of the bridge 730. The metatarsal or transverse arch supports the void under the lower surface of the foot directly behind the metetarsal bones. Normally this area rarely touches the ground unless an individual suffers from a collapsed transverse arch. Once identified a supporting device can be integrated with the footbed of the present invention.

Although the invention has been described and illustrated with a certain degree of particularity, it is understood that the present disclosure has been made only by way of example and that numerous changes in the combination and arrangement of parts can be resorted to by those skilled in the art without departing from the spirit and scope of the invention.

The modular footbed design shown above is but one of a plurality of possible implementations of a modular concept. The present invention addresses not only lateral and medial deviation of the knee due to ankle misalignment from a varus or valgus forefoot deviation but also inclination issues as well as the ability to address asymmetrical variations in a person's foot. Other implementations of the concepts presented herein are certainly possible and are indeed contemplated by the applicant.

To properly construct the modular footbed of the present invention an accurate and realistic assessment of an individual's foot/ankle/knee alignment or misalignment must be gained. Critical to this assessment is the understanding of the distinction between a static assessment and a dynamic assessment. Many, but not all, misalignment issues of the skeleton and musculature are minimized when the body is in a static condition or simply standing still. There are certainly individuals who have varus and valgus deviations when standing with both feet on the ground. These conditions are more structural in nature than neuromuscular. However many individuals can have little indications of varus or valgus deviation, or for that matter over or under pronation, when they are statically standing still yet have significant problems when walking or running.

Figure 10:
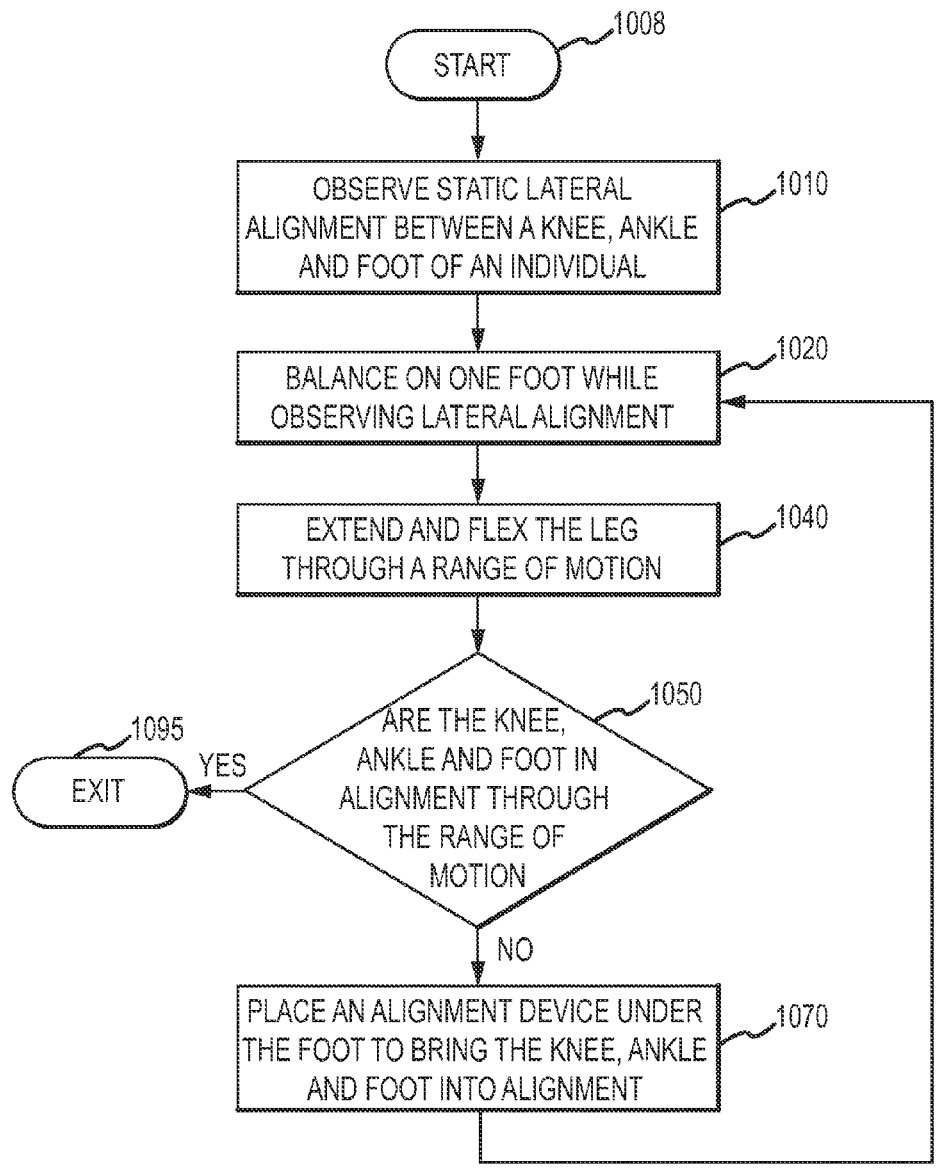
FIG. 10 is a flowchart of one method embodiment of the present invention for determining dynamic angular deviation.

According to one embodiment of the present invention, lateral deviation or misalignment can be determined by dynamically assessing each limb separately. FIG. 10 is a flowchart depicting an example of the methodology which may be used to determine lateral misalignment of a limb. In the following description, it will be understood that each block of the flowchart illustrations, and combinations of blocks in the flowchart illustrations, can be implemented by computer program instructions or similar device. These instructions may be loaded onto a computer or other programmable apparatus to produce a machine such that the instructions that execute on the computer or other programmable apparatus create means for implementing the functions specified in the flowchart block or blocks. These instructions may also be stored in a computer-readable memory that can direct a computer or other programmable apparatus to function in a particular manner such that the instructions stored in the computer-readable memory produce an article of manufacture including instruction means that implement the function specified in the flowchart block or blocks. The instructions may also be loaded onto a programmable apparatus to cause a series of operational steps to be performed to produce a process such that the instructions that execute on the programmable apparatus provide steps for implementing the functions specified in the flowchart block or blocks.

Accordingly, blocks of the flowchart illustrations support combinations of means for performing the specified functions and combinations of steps for performing the specified functions. It will also be understood that each block of the flowchart illustrations, and combinations of blocks in the flowchart illustrations, can be implemented by special purpose hardware-based systems that perform the specified functions or steps, or combinations of special purpose hardware including computer instructions. For example, while the identification and measurement of lateral deviation has been described in the aforementioned text by way of visually monitoring the motion and track of a limb as it is moved throughout its range of motion, other means can be used by which to determine whether the knee remains in alignment during bipedal motion. Musculature definition, development and functionality may also indications of misalignment. One of reasonable skill in the relevant art will appreciate that there are many ways by which to measure lateral deviation without departing from the scope of the present invention According to one embodiment of the present invention a lateral deviation assessment begins 1008 with observing static lateral alignment 1010 between the knee, ankle and foot of an individual. The alignment is measured from a base line between the femoral head and the talus of the heel bone. From that point the individual is asked to balance 1020 on one foot while any change in lateral deviation is observed.

While balancing on one foot the individual extends and flexes 1040 the knee through a range of motion in what is akin to a single leg squat. To the extent that the individual can complete a partial single leg squat, the side-to-side movement of the knee should be noted with respect to the base line as it translates up and down. If the individual cannot complete a single leg squat then a quarter squats should be attempted. It is desirable to assess alignment without providing additional balance or lifting support.

As the individual flexes and extends the leg movement of the knee is observed to determine whether the knee is in alignment with the hip and ankle 1050. In addition to observing lateral displacement of the knee during flexion and extension, the activity of the musculature surrounding the ankle and foot are observed. As was previously described, bipedal motion is a complex interaction of musculature and skeletal activities. Contractions of the musculature that is balanced in both intensity and duration is representative of neutral alignment while an unbalanced series of contractions is indicative of a deviation. According to one embodiment of the present invention alignment can be determined by examination of the intensity and duration of muscle contractions during a dynamic examination.

When the knee moves either laterally or medially a corresponding modular alignment device is placed under the foot 1070 to bring the ankle, foot and knee into alignment. With the device in place the individual once again balances on one foot 1020 and extends and flexes their leg 1040. Again alignment is assessed 1050 to see whether there is any lateral or medial deviation. Measuring, flexing and extending with differing inserts continues iteratively until during a subsequent flexure and extension motion the knee remains aligned with the base line. The process ends 1095 when dynamic alignment is achieved. Once the measurements for a modular footbed have been determined for one leg, the same dynamic analysis is conducted for the other leg. As one of reasonable skill can appreciated there is likely to be differences in the correction necessary for each leg so alignment for each leg much be considered independently.

Having gained a lateral/medial as well as an anterior/posterior measurement a modular footbed can be constructed to meet the measurement. The dynamic nature of the measurement process of the present invention captures the interaction between the knee, ankle and foot through the motions of the leg. As one of reasonable skill in the relevant art will appreciate, a single static measurement is inadequate to capture how various deviations and individual characteristics control the alignment of the knee as it flexes and extends. As an individual walks or runs each leg operates independently to carry the body forward. While a static measurement can give some insight as to structural (skeletal) deviation of the lower extremities, a dynamic test mimicking walking or running identifies lateral or medial deviations resulting from a combination of factors. In essence the entire systems, skeletal, neuromuscular, and proprioceptive are evaluated. From that evaluation a modular footbed can be constructed that places the foot, ankle and knee in alignment, not only statically but also dynamically.

Using the lateral/medial and anterior/posterior measurements that place each leg independently into neutral dynamic alignment a certain degree of normal pronation can be set into the footbed. According to another embodiment of the present invention, the information gained for the dynamic testing of each leg can provide a basis by which to develop footbeds that can facilitate or enhance performance for certain activities.

Using a formula and the measurements referenced above, a neutral pronation datum can be determined. From that datum, predetermined sets of pronation can be set into specific footbeds that are specific for particular types of activities. For example, the amount of pronation set in a footbed used in conjunction with skiing can be for the same individual different than for running. Likewise, an individual who is likely to be doing explosive accelerations such as in tennis can use a different set of footbeds designed for that specific sport. The development of a neutral pronation datum enables a plurality of sport specific footbeds to be designed and provided for each individual. Each footbed can be tailored for both the individual and the type of activity As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Moreover, as used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Upon reading this disclosure, those of skill in the art will appreciate still additional alternative structural and functional designs for a modular footbed and a process for determining lateral alignment of a lower extremity through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

The invention claimed is:

1. A method for lateral ankle alignment, comprising:
observing lateral alignment between a foot, knee and corresponding ankle of an individual while elevating the other foot, wherein observing occurs while the foot is static; and
responsive to observing lateral misalignment between the foot, knee, and corresponding ankle of the individual, placing an alignment device under the foot of the individual so as to bring the foot, knee, and corresponding ankle into alignment.

2. The method of claim 1 wherein observing includes iterative knee articulation associated with the foot and corresponding ankle and detecting lateral displacement during said articulation.

3. The method of claim 2 wherein lateral knee displacement indicates misalignment of the foot and corresponding ankle.

4. The method of claim 1 wherein observing occurs while the individual dynamically extends and flexes the foot, knee and corresponding ankle.

5. The method of claim 4 wherein observing includes detecting lateral knee displacement while flexing and extending.

6. The method of claim 4 wherein observing includes detecting opposing musculature recruitment.

7. The method of claim 4 wherein observing include detecting a range of lateral motion.

8. The method of claim 1 wherein observing includes measuring lateral displacement of the knee during extension and flexion.

9. The method of claim 1 wherein the alignment device is modular including forefoot and heel components that independently operable to correct forefoot and heel lateral misalignment.

10. The method of claim 1 wherein the alignment device includes one or more angled footbeds.

11. The method of claim 10 wherein the one or more angled footbeds are tapered along the length of the foot.

12. The method of claim 11 wherein thickness of the one or more footbeds are minimized so as to minimize toe-shoe interaction.

13. The method of claim 1 wherein the alignment device includes a bridge interfacing between a forefoot component and a heel component.

14. The method of claim 1 wherein the alignment device includes a modular arch support.

15. The method of claim 1 wherein the alignment device includes a transverse arch support.

16. The method of claim 1 wherein the alignment device includes inclination corrective components.

17. A method for lateral ankle alignment, comprising:
measuring lateral alignment between a knee, a foot and corresponding ankle of an individual while the individual balances on the foot; and
modifying alignment of the knee, foot and corresponding ankle to a neutral position.

18. The method of claim 17 further comprising elevating the other foot while balancing on the foot.

19. The method of claim 17 further comprising dynamically extending and flexing the knee iteratively while balancing on the foot.

20. The method of claim 19 further comprising detecting lateral displacement of the knee during extension and flexion of the knee.

21. The method of claim 17 wherein modifying includes placing an alignment device under the foot to bring the foot, knee and corresponding ankle to the neutral position.

22. The method of claim 21 wherein the alignment device is modular including independent forefoot and heel components operable to correct forefoot and heel lateral misalignment in Varus or Valgus.

23. The method of claim 22 wherein the forefoot and heel components are operable to correct forward and rearward ankle articulation.

24. The method of claim 22 wherein the alignment device includes one or more footbeds of varying lateral inclination.

25. The method of claim 24 wherein the one or more footbeds are tapered along the length of the foot.

26. The method of claim 24 wherein thickness of the one or more footbeds are minimized so as to minimize toe-shoe interaction.

27. The method of claim 21 wherein the alignment device includes a bridge interfacing between a forefoot and a heel component.

28. The method of claim 27 wherein the alignment device includes a modular arch support coupled to the bridge.

29. The method of claim 21 wherein the alignment device includes a transverse arch support.

* * * * *